United States Patent
Lamensdorf et al.

(10) Patent No.: US 11,266,701 B2
(45) Date of Patent: *Mar. 8, 2022

(54) SYNERGISTIC COMBINATIONS OF CAFFEINE, GINKGO BILOBA AND BETA-PHENYLETHYLAMINE

(71) Applicant: TRINUTRA LTD., Nes Ziona (IL)

(72) Inventors: Itschak Lamensdorf, Modi'in (IL); Yoram Sela, Ra'anana (IL); Mor Zeilkha, Ramat Gan (IL)

(73) Assignee: TRINUTRA LTD., Nes Ziona (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/188,613

(22) Filed: Nov. 13, 2018

(65) Prior Publication Data
US 2019/0076495 A1 Mar. 14, 2019

Related U.S. Application Data (63) Continuation of application No. 15/841,830, filed on Dec. 14, 2017, now Pat. No. 10,159,702, which is a continuation of application No. PCT/IL2017/050733, filed on Jun. 29, 2017.

(60) Provisional application No. 62/367,792, filed on Jul. 28, 2016.

(51) Int. Cl.
| | | |
|---|---|---|
| *A61K 36/16* | (2006.01) | |
| *A61K 36/77* | (2006.01) | |
| *A61K 9/20* | (2006.01) | |
| *A61K 31/137* | (2006.01) | |
| *A61K 31/522* | (2006.01) | |
| *A61K 36/258* | (2006.01) | |
| *A61K 36/484* | (2006.01) | |
| *A61K 45/06* | (2006.01) | |

(52) U.S. Cl.
CPC .......... *A61K 36/16* (2013.01); *A61K 9/2009* (2013.01); *A61K 9/2054* (2013.01); *A61K 31/137* (2013.01); *A61K 31/522* (2013.01); *A61K 36/258* (2013.01); *A61K 36/484* (2013.01); *A61K 36/77* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 7,674,482 B2 * | 3/2010 | Shell | A61K 31/522 424/439 |
| 9,526,793 B1 | 12/2016 | Kramer et al. | |
| 10,159,702 B2 * | 12/2018 | Lamensdorf | A61K 36/484 |
| 2006/0134181 A1 | 6/2006 | Altaffer et al. | |
| 2006/0159726 A1 | 7/2006 | Shell et al. | |
| 2015/0132280 A1 | 5/2015 | Lopez et al. | |
| 2016/0038552 A1 | 2/2016 | Bredesen et al. | |
| 2016/0213673 A1 | 7/2016 | Bartos et al. | |

FOREIGN PATENT DOCUMENTS

| | | |
|---|---|---|
| WO | WO 2017/125924 | 7/2017 |

OTHER PUBLICATIONS

International Search Report issued in PCT/IL2017/050733 dated Sep. 11, 2017.
Abdo A. Rock-Star and Other Shockingly Uncommon Causes of Pancreatitis. HPB 15(Suppl 1)Feb. 1, 2013.
Belviranli et al., "Age, Sex and Anxiety Affect Locomotor Activity in Rats" *Proceedings of Measuring Behavior*(Utrecht, The Netherlands, Aug. 28-31, 2012), pp. 500-503.
Caballero et al., "Caffeine improves attention deficit in neonatal 6-OHDA lesioned rats, an animal model of attention deficit hyperactivity disorder (ADHD)" *Neuroscience Letters*, 494 (2011) 44-48.
Irsfeld et al. "Beta-phenylethylamine, a small molecule with a large impact" WebmedCentral *Biochemistry*, 2013; 4(12):WMC004459.
Moscardo et al., "The Novel Object Recognition Test in Rodents: Which are the Essential Methodological Aspects" *Proceedings of Measuring Behavior* (Utrecht, The Netherlands, Aug. 28-31, 2012), pp. 476-478.
Scholey A. et al. Cognitive and Physiological Effects of an Energy Drink. Psychopharmacology 176(3-4)320-330, Nov. 2004.
Shadfar et al., "Involvement of inflammation in Alzheimer's disease pathogenesis and therapeutic potential of anti-inflammatory agents" *Arch. Pharm. Res.*, Review, Aug. 21, 2015, 15 pages, DOI 10.1007/s12272-015-0648-x.
Uebel-von Sandersleben et al., "Originalarbeit—Ginkgo biloba Extract EGb 761® in Children with ADHD; Preliminary Findings of an Open Multilevel Dose-Finding Study" *Zeitschrift für Kinder— und Jugendpsychiatrie und Psychotherapie*, 42 (5), 2014, 337-347.
Verlaet et al., "Nutrition, immunological mechanisms and dietary immunomodulation in ADHD" *Eur Child Adolesc Psychiatry*, Review, Feb. 4, 2014, Springer, 11 pages, DOI 10.1007/s00787-014-0522-2.
Verna R. The History and Science of Chocolate. Malaysian J of Pathology 35(2) 111-121, Dec. 2013.
Weiss et al., "A Guide to the Treatment of Adults with ADHD" *J Clin Psychiatry*, 2004; 65 (suppl 3).

* cited by examiner

*Primary Examiner* — Ralph J Gitomer
(74) *Attorney, Agent, or Firm* — Nixon & Vanderhye P.C.

(57) ABSTRACT

The present invention provides a therapeutic composition comprising a synergistic combination of caffeine, *Ginkgo biloba*, and β-phenylethylamine (PEA) or its salt. The invention is also directed to oral dosage forms containing said composition, and to a method of treatment of a psychological, psychiatric, behavioral and/or neurodevelopmental disorder comprising the administration of said compositions and dosage forms to a patient in need thereof.

17 Claims, 7 Drawing Sheets

SYNERGISTIC COMBINATIONS OF CAFFEINE, GINKGO BILOBA AND BETA-PHENYLETHYLAMINE

This application is a continuation of application Ser. No. 15/841,830 filed Dec. 14, 2017, now U.S. Pat. No. 10,159, 702, issued Dec. 25, 2018, which is a continuation of International Application No. PCT/IL2017/050733 filed Jun. 29, 2017, which designated the U.S. and claims the benefit of Provisional Application No. 62/367,792 filed Jul. 28, 2016, the entire contents of each of which are hereby incorporated by reference.

BACKGROUND OF THE INVENTION

Psychological and behavioral disorders such as ADHD, are mostly treated with synthetic drugs or combinations of synthetic drugs.

Attention deficit hyperactivity disorder (ADHD) is a behavioral disorder affecting about 4-12% of children, beginning by age six to twelve and manifesting itself by attention, hyperactivity or impulsive acting problems. ADHD continues into adulthood for approximately 50% of those diagnosed in childhood (J. Clin. Psychiatry 2004; 65[suppl 3]:27-37), M. D. Weiss). Boys are diagnosed with ADHD three times more than girls.

A significant percentage of children diagnosed with ADHD continue to suffer from its symptoms also as adults, one of the main symptoms being restlessness.

Generally, ADHD is managed by one or more of counseling, lifestyle changes and medication.

Medication for ADHD includes treatment with stimulants such as methylphenidate and amphetamines. In addition, non-stimulants such as atomoxetine, guanfacine and clonidine may also be used.

Commercial ADHD stimulant drugs include: Adderall and Adderall XR, Concerta, Dexedrine, Focalin and Focalin XR, Metadate CD and Metadate ER, Methylin and Methylin ER, Ritalin, Ritalin SR, Ritalin LA, Vyvanse, Daytrana and Quillivant XR. Only some of the above drugs are FDA-approved for use in adults.

Non-stimulant ADHD drugs include Strattera, Intuniv and Kapvay.

When stimulants and nonstimulants are not effective or well-tolerated or when certain conditions are present, several other medications are available to treat ADHD. These medications include: Elavil, Norpramin, Pamelor, Tofranil or other tricyclic antidepressants, Catapres, Duraclon, Nexiclon, Tenex, Wellbutrin.

All the above drugs are single or fixed dose combinations of synthetic drugs.

Common side-effects of the above drugs include: decreased appetite, weight loss, sleep problems, headaches and jitteriness. In addition, sometimes more serious side-effects are observed, like an increased risk of cardiovascular problems.

The multitude of the drugs used for ADHD treatment highlights the fact that there is no single drug which is both highly effective and devoid of side-effects.

In addition to ADHD, other disorders with psychological and/or behavioral components in need of a herbal composition treatment include depression, autism, mood disorders, posttraumatic stress disorder, cognitive impairment (such as in Alzheimer's disease) and motor neurodegenerative diseases (such as Parkinson's disease).

There is thus an unmet need for a highly effective herbal treatment for disorders of this type, especially ADHD in both children and adults, that is essentially devoid of side-effects.

SUMMARY OF THE INVENTION

The invention relates to novel compositions comprising synergistic fixed dose combinations of natural substances. More specifically, the invention relates to herbal fixed dose combinations (FDC) of therapeutically effective doses of *Ginkgo biloba*, β-phenylethylamine (PEA; also known as phenethylamine) and caffeine, optionally with the addition of one or more additional herbal actives, including, but not limited to, guarana, ginseng, kaempferol, curcumin, licorice, Amur Corktree (*Phellodendron amurense*), licorice root (*Glychrrhiza glabra* and *Glycyrrhiza uralensis*), Psoralea Fruit (*Psoralea corylifolia*) and Bakuchi seed (*Cyamposis psoralioides*).

The present invention is also directed to oral dosage forms (such as tablets, capsules, caplets, powders and liquids) that are suitable for the oral delivery of the compositions of the present invention to human subjects.

In another aspect, the present invention is directed to methods of treatment of behavioral, psychological and/or psychiatric disorders, in particular ADHD, by means of administering therapeutically effective doses of the above-defined synergistic compositions to subjects in need of such treatment.

It has been surprisingly found that in addition to having the abovementioned beneficial effects on psychological and psychiatric conditions such as ADHD, the above-defined compositions also possess significant anti-inflammatory activity. As will be shown hereinbelow, the various natural products present in the compositions interact synergistically in producing the anti-inflammatory effect.

The present invention also encompasses methods of treating inflammatory disorders by means of administering therapeutically effective doses of these compositions to subjects in need of such treatment.

DETAILED DESCRIPTION OF THE PRESENT INVENTION

This invention provides synergistic natural substance compositions, which are characterized both by their ability to treat a number of psychological and psychiatric disorders (such as ADHD) and by their anti-inflammatory properties. With regard to the first of these two characteristics, it is to be noted that inter alia, the presently disclosed compositions possess amphetamine-like and cognitive enhancing activities.

While many synthetic drugs currently used to treat ADHD—such as Ritalin and Ritalin-like drugs—are based on amphetamine or its derivatives, the currently claimed product is based on a combination of only natural products, primarily *Ginkgo biloba*, β-phenylethylamine (PEA) or its salt and caffeine. Optionally, the present composition may further comprise one or more other herbal actives including, but not limited to, guarana, ginseng and kaempferol.

The aforementioned guarana contains several stimulants belonging to the xanthine family: caffeine, theophylline and theobromine. It is to be noted that there are mixed data regarding the value and potential benefit of guarana as the sole therapeutic agent in the treatment of ADHD and other psychological or psychiatric disorders. In view of the xanthine content of guarana, this herbal active may be incorporated into the compositions of the present invention in place of other caffeine sources.

The herbal actives used in the compositions of the present invention are standardized herbal extracts, whenever available.

It is to be noted that the plant-derived material used in the manufacture of the compositions of the present invention (e.g. *Ginkgo biloba*-containing plant material and caffeine-containing plant material such as green tea or guarana) is obtained in any of the various forms well known to the skilled artisan in this field, including: dried plant material obtained from roots, leaves, shoots, flowers and whole plants; aqueous and non-aqueous extracts; teas or tisanes; decoctions and tinctures; oils.

The caffeine used in the compositions of the present invention may be obtained from any suitable and convenient source including, but not limited to, coffee beans, black tea, green tea and guarana (*Paullinia cupana*, also known as *P. crysan* or *P. sorbilis*).

As disclosed hereinabove, the present invention is primarily directed to a composition comprising three main active ingredients: caffeine, *Ginkgo biloba* and β-phenylethylamine (PEA), the latter typically in the form of the base or its salt, typically the hydrochloride salt.

Preferably said composition comprises a synergistic combination of the three above-mentioned active ingredients. That is, said ingredients are present in the composition in amounts and in mutual weight or molar ratios such that there is a synergistic interaction between said ingredients, as measured on at least one experimental or clinical model. For the purpose of the present disclosure, the term "synergistic" is used to indicate that the results obtained for a particular biological effect using a combination of active ingredients are greater than additive—that is, greater than the sum of the results for each ingredient alone.

In some embodiments, the composition may optionally further comprise additional pharmacologically-active ingredients, including (but not limited to) the group consisting of guarana, ginseng, kaempferol, curcumin, licorice, Amur Corktree (*Phellodendron amurense*), licorice root (*Glychrrhiza glabra* and *Glycyrrhiza uralensis*), Psoralea Fruit (*Psoralea corylifolia*) and Bakuchi seed (*Cyamposis psoralioides*) and combinations thereof.

The compositions of the present invention are primarily intended for use as therapeutic compositions in the treatment or management of various diseases and disorders, as will be described in more detail, hereinbelow.

In one embodiment, the composition of the invention preferably comprises the three main ingredients disclosed above in a weight in the range of 1 caffeine: 0.1-10 *Ginkgo biloba:* 1-15 PEA.

In one embodiment, the composition of the invention preferably comprises the three main ingredients in a weight ratio in the range of 1 caffeine: 2-8 *Ginkgo biloba:* 1.5-5 PEA.

In one embodiment, the composition of the invention preferably comprises the three main active ingredients in a weight ratio in the range of 1 caffeine: 0.1-6 *Ginkgo biloba:* 1.6-12.5 PEA.

In another embodiment, the composition of the invention preferably comprises the three main active ingredients in a weight ratio of 1 caffeine: 6 *Ginkgo biloba:* 3 PEA.

In one embodiment, the weight ratio between PEA and *Ginkgo biloba* is between about 0.1:1 and 20:1. Typically, the PEA/*Ginkgo biloba* ratio is in the range of about 0.5:1 to 16:1.

In one particular embodiment, the weight ratio between PEA and *Ginkgo biloba* is 0.5:1.

The ratio between PEA and caffeine is between about 1:1 and 20:1. Typically, the PEA/caffeine ratio is in the range of about 1.5:1 to 15:1.

In one particular embodiment, the ratio between PEA and caffeine is 3:1.

The novel FDC compositions of the instant invention comprise a fixed dose combination of *Ginkgo biloba* and PEA or its salt, caffeine and pharmaceutically acceptable excipients. The typical PEA salt is the hydrochloride. Throughout this disclosure, the term PEA is to be understood to include both the PEA base and its salts.

While the composition component ratios indicated here are believed to be effective, the actual component ratios in the compositions will be selected as a result of detailed clinical studies and titration in humans using known methods.

The compositions of the present invention may be administered to a patient in need thereof once, twice or more daily, in the form of tablets, caplets, capsules, liquids, syrups or powder (sachets) or dispersible tablets for suspension to be added to water.

The compositions of this aspect of the present invention may also be formulated in several different other dosage forms for administration to mammalian (particularly human) subjects. Suitable dosage forms include (but are not limited to) oral dosage forms (as mentioned above), sub-lingual dosage forms, injectable formulations, suppositories, patches for use on skin or mucous membranes, inhalable formulations, topical formulations and so on. Further details of the preparation of such formulations and dosage forms can be obtained from any standard reference on the subject, such as Remington's Pharmaceutical Sciences, Mack Publishing Co, Easton, Pa., USA, 21$^{st}$ edition (2006).

The novel compositions of the instant invention may be formulated in various formulation options, such as for example:

1. Immediate release of all the components (see Example 2)
2. Extended release of part of *Ginkgo biloba* and immediate release of the other components (see Example 3)
3. Extended release of all *Ginkgo biloba* and immediate release of the other components (see Example 4).
4. Enteric coated dosage forms of the above (see Example 5)

Since *Ginkgo biloba* has a half-life of about 4.5 hours the *Ginkgo* component (all or part of it) may be provided as controlled release granules which will provide a prolonged release pattern for the *Ginkgo biloba*. For example, in a unit dose containing 75 mg *Ginkgo biloba*, 50 mg will be controlled release and 25 mg immediate release. Alternatively, half of the *Ginkgo biloba* dosage will be controlled release and the other half immediate release.

In one aspect, the present invention is directed to an oral dosage form comprising the composition disclosed above, that is, a composition that comprises caffeine, *Ginkgo biloba* and PEA. The term "oral dosage form" is to be understood to refer to a product which is to be administered to a patient, and which therefore may include, in addition to the aforementioned active ingredients, pharmaceutical excipients (e.g. fillers, stabilizers, anti-oxidants, release-control polymers, and so on). The term "unit dose" is to be understood to refer to a single unit of the dosage form—that is, a single capsule, caplet, tablet and so on. Of course, whenever smaller doses are required, it is possible to divide a single unit dose, for example by means of cutting a tablet or caplet into two halves, using a pill cutter or knife blade.

In one embodiment, the oral dosage form of the present invention comprises 30-200 mg of caffeine per unit dose.

In one embodiment, the oral dosage form comprises 30-200 mg caffeine, 50-500 mg *Ginkgo biloba* and 50-1000 mg PEA, per unit dose.

In one embodiment, the oral dosage form comprises 40-100 mg caffeine, 100-400 mg *Ginkgo biloba* and 100-200 mg PEA, per unit dose.

In one particular embodiment, the oral dosage form comprises 50 mg caffeine, 300 mg *Ginkgo biloba* and 150 mg PEA, per unit dose.

In some embodiments, all of the active components of the composition are formulated for immediate release. In other embodiments, at least some of the active components are formulated for controlled (e.g. delayed, extended or sustained) release by combining those components with a release-control polymer, or the like, as is well known in the art. In some embodiments of this type, either a portion or all of the *Ginkgo biloba* in the dosage form is formulated for controlled release.

In some embodiments, the oral dosage forms of the present invention also comprise an enteric coating.

In another aspect, the present invention encompasses a method of treatment of a psychological, psychiatric, behavioral and/or neurodevelopmental disorder comprising the administration of therapeutically effective doses of compositions of the instant invention to a patient in need thereof.

In one embodiment of the method of treatment defined immediately hereinabove, the composition is administered in an amount such that the daily dosage of each active component is in the range of 10-200 mg caffeine, 20-1000 mg *Ginkgo biloba* and 30-600 mg PEA.

In one embodiment of this method, the composition is administered in an amount such that the daily dosage of each active component is 50 mg caffeine, 300 mg *Ginkgo biloba* and 150 mg PEA.

In other embodiment of this method, the composition is administered in an amount such that the daily dosage of each active component is 100 mg caffeine, 600 mg *Ginkgo biloba* and 300 mg PEA.

In other embodiment of this method, the composition is administered in an amount such that the daily dosage of each active component is 150 mg caffeine, 900 mg *Ginkgo biloba* and 450 mg PEA.

In other embodiment of this method, the composition is administered in an amount such that the daily dosage of each active component is 25 mg caffeine, 150 mg *Ginkgo biloba* and 75 mg PEA.

In a still further embodiment of this method, the composition is administered in an amount such that the daily dosage of each active component is approximately 12.5 mg caffeine, 75 mg *Ginkgo biloba* and 37.5 mg PEA.

In one embodiment of this method of treatment, the patient is a child.

In another embodiment of this method, the patient is an adult.

In one embodiment of the above-defined of method of treatment, the psychological, psychiatric, behavioral and/or neurodevelopmental disorder is selected from the group consisting of attention deficit-related disorders such as attention deficit hyperactivity disorder (ADHD) and attention deficit disorder (ADD), depression, autism, mood disorders in general, posttraumatic stress disorder, cognitive impairment such as Alzheimer's disease and motor neurodegenerative diseases such as Parkinson's disease.

In one particular embodiment, the disorder to be treated is ADHD.

The present invention is also directed to the above-defined compositions and oral dosage forms for use in the treatment of a psychological, psychiatric, behavioral and/or neurodevelopmental disorder.

In another aspect, the present invention is also directed to a method of treating a disease or disorder having an inflammatory component.

In one embodiment of this aspect, the disease or disorder to be treated has an inflammatory component which is at least in part mediated by nitric oxide (NO).

In one embodiment, the disease or disorder having an inflammatory component is selected from the group consisting of acute inflammatory conditions, chronic inflammatory conditions, osteoarthritis rheumatoid arthritis, inflammatory conditions of the upper and lower respiratory tracts (including asthma), peritonitis, cardiovascular inflammation, sepsis, trauma, inflammation of the skin (such as in psoriasis, acne, dermatitis and so on), inflammatory conditions of the central and/or peripheral nervous systems and various types of gastrointestinal inflammation. This list is, of course, not exhaustive and is provided for exemplary purposes only.

The present invention is also directed to the above-defined compositions and oral dosage forms for use in the treatment of diseases or disorders having an inflammatory component.

The compositions, dosage forms and methods of the present invention are highly effective in the treatment of disorders having psychological, psychiatric, behavioral, neurodevelopmental and inflammatory aspects. In addition to their high efficacy, the present compositions also cause significantly fewer side effects than existing pharmaceutical agents. They therefore may be used to replace the existing synthetic drugs and drug combinations.

EXAMPLES

The following examples illustrate certain embodiments of the invention but are not meant to limit the scope of the claims in any way. The following examples are put forth so as to provide those of ordinary skill in the art with a complete disclosure and description of how to make and use the described invention, and are not intended to limit the scope of what the inventors regard as their invention nor are they intended to represent that the experiments below are all or the only experiments performed or designed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

The following four types of working example are presented in the sections that follow:

I In vitro studies demonstrating the anti-inflammatory properties of the presently-disclosed compositions.
II Formulation examples.
III Preclinical studies concerning the treatment of psychological/psychiatric disorders in laboratory animals.
IV Pilot clinical study concerning the treatment of ADHD.

I. In Vitro Studies Demonstrating the Anti-Inflammatory Properties of the Presently-Disclosed Compositions Example 1

Introduction:

The three obligatory components of the claimed composition were tested in an in vitro model of inflammation (nitric oxide (NO) production), in order to determine whether said components possess anti-inflammatory activity when tested individually and/or in combination.

Methods:

$10^5$ cells from a murine macrophage cell line, RAW 264.7, were seeded in 96-well plates in a medium containing 1% FBS, 1% Glutamine and 1% Pen/strep in DMEM. The cells were then treated with either Caffeine (40 µg/ml), Ginkgo biloba (240 µg/ml), PEA (120 or 240 µM) or their combination (Ginkgo+PEA+Caffeine) at the indicated concentrations for 22 hours, together with LPS induction (5 ng/ml). In addition, positive control cells were treated with 20 µM dexamethasone. Nitric oxide (NO) release was tested after incubation at 37° C., 5% $CO_2$ using the Griess Reagent System. The method is based on the chemical diazotization reaction that was originally described by Griess in 1879, which uses sulfanilamide and N-1-napthylethylenediamine dihydrochloride (NED) under acidic (phosphoric acid) conditions. This system detects $NO_2^-$ in a variety of biological and experimental liquid matrices such as tissue culture medium that was tested in this study.

Figure 1:
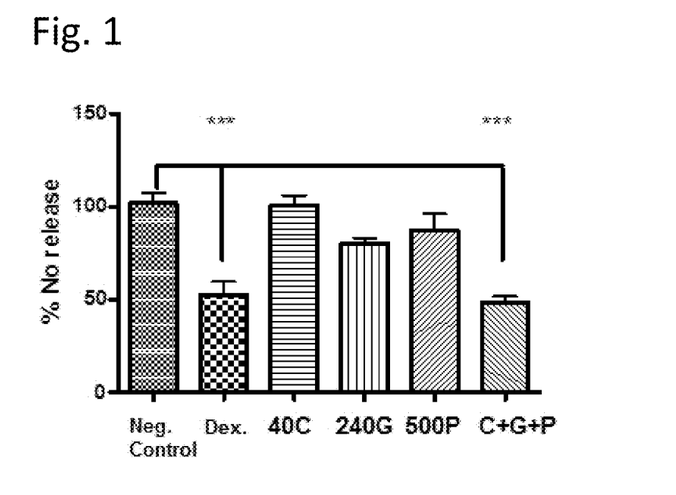
FIG. 1 graphically presents results that indicate a synergistic anti-inflammatory effect of a composition of the invention comprising 40 µg/ml caffeine, 240 µg/ml *Ginkgo biloba* and 500 µg/ml PEA.

Results:

Combinations of caffeine, Ginkgo biloba and PEA were tested at the following concentrations, with the results of their effects on NO production shown in the indicated figures:

FIG. 1:
40 µg/ml caffeine
240 µg/ml Ginkgo biloba
500 µg/ml PEA
Caffeine:Ginko blowpipes weight ratio=1:6:12.5

Figure 2:
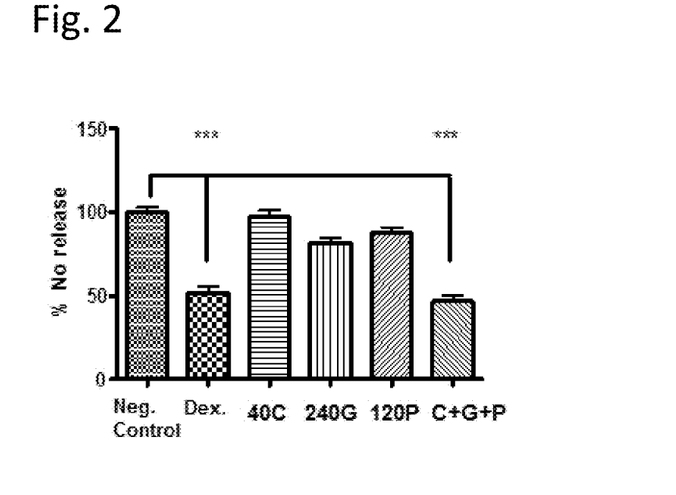
FIG. 2 graphically presents results that indicate a synergistic anti-inflammatory effect of a composition of the invention comprising 40 µg/ml caffeine, 240 µg/ml *Ginkgo biloba* and 120 µg/ml PEA.

FIG. 2:
40 µg/ml caffeine
240 µg/ml Ginkgo biloba
120 µg/ml PEA
Caffeine:Ginko biloba:PEA weight ratio=1:6:3

Figure 3:
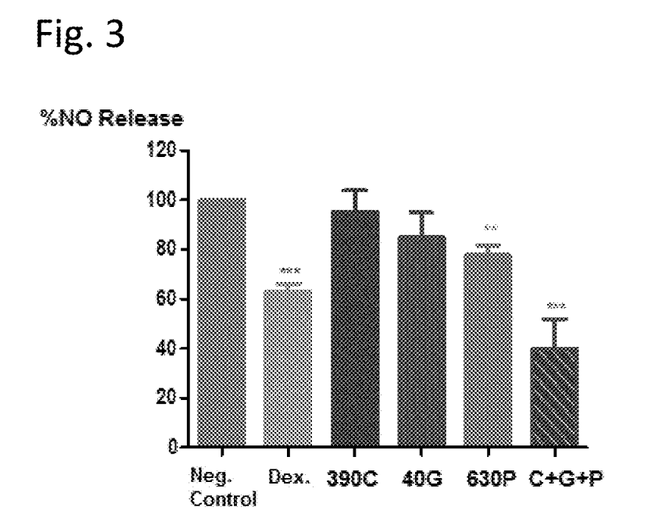
FIG. 3 graphically presents results that indicate a synergistic anti-inflammatory effect of a composition of the invention comprising 390 µg/ml caffeine, 40 µg/ml *Ginkgo biloba* and 630 µg/ml PEA.

FIG. 3:
390 µg/ml caffeine
40 µg/ml Ginkgo biloba
630 µg/ml PEA
Caffeine:Ginko biloba:PEA weight ratio=1:0.1:1.6

It may be seen from FIG. 1 that while 40 µg/ml caffeine (40C) was essentially without effect on NO release from the cultured cells, both 240 µg/ml Ginkgo biloba (240G) and 500 µg/ml PEA (500P), when tested separately, caused a reduction in NO release to about 80% and 85%, respectively, of the LPS-only negative control ("Neg. Control") values. However, when all three agents were combined at the indicated concentrations (C+G+P), the reduction in NO release (55%) was much greater than the predicted additive value of the reduction for all three agents together (0+20+15=35%). Statistical analysis using one-way ANOVA confirmed that only the three agents in combination and the dexamethasone positive control ("Dex.") caused a change in NO release from negative control that was highly significant (*** $P<0.001$).

It may be seen from FIG. 2 that while 40 µg/ml caffeine (40C) was essentially without effect on NO release from the cultured cells, both 240 µg/ml Ginkgo biloba (240G) and 120 µg/ml PEA (120P), when tested separately, caused a reduction in NO release to 80% and 95%, respectively, of the LPS-only negative control ("Neg. control") values. However, when all three agents were combined (C+G+P) at the same concentrations as when tested individually, the reduction in NO release (54%) was much greater than the predicted additive value of the reduction for all three agents together (0+20+15=35%). Statistical analysis using one-way ANOVA confirmed that only the three agents in combination and the dexamethasone positive control ("Dex.") caused a change in NO release from negative control that was highly significant (*** $P<0.001$).

Finally, it may be seen from FIG. 3 that 390 µg/ml caffeine (390C) and 40 µg/ml Ginkgo biloba (40G) each caused a slight reduction in NO release, in relation to the negative control ("Neg. control"), when tested separately. However, the reduction in NO release caused by 630 µg/ml PEA (630P) was larger 20% reduction) and reached statistical significance ($P<0.05$) when compared with the negative control. When all three agents were combined (C+G+P) at the same concentrations as when tested individually, the reduction in NO release (60%) was much greater than the predicted additive value of the reduction for all three agents together (5+15+20=40%). Statistical analysis using one-way ANOVA confirmed that only the three agents in combination and the dexamethasone positive control ("Dex.") caused a change in NO release from negative control that was highly significant (*** $P<0.001$).

In order to further investigate the synergism between the three active components described above, binary combinations (i.e. pairs) of said components were tested on the same NO release system, using the same concentration of each active component as in the experiments used to generate FIG. 3. The results of these investigations are shown in FIGS. 4 to 6.

Figure 4:
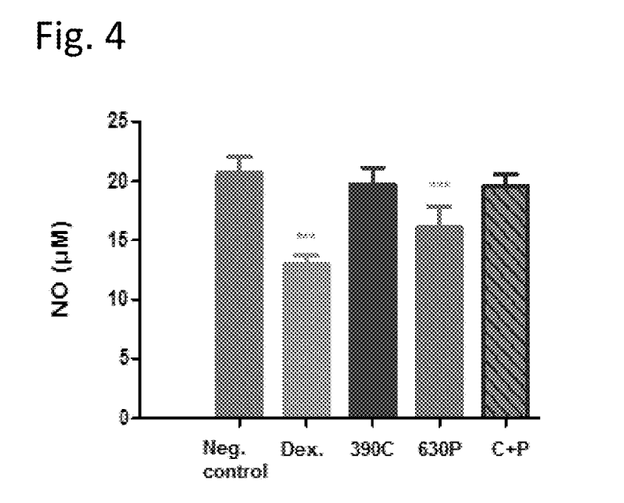
FIG. 4 presents the results for a binary combination of caffeine and PEA at the same concentrations as used to generate the results for the synergistic three-component composition in FIG. 3.

It may be seen from FIG. 4 that although 630 µg/ml PEA does cause a significant reduction in NO release ($p<0.001$), when tested alone, this reduction was considerably less than that seen in the positive control (dexamethasone)—as opposed to the three-component combination which displayed a greater effect than dexamethasone in this model (see FIG. 3). Furthermore, a combination of 390 µg/ml caffeine and 630 µg/ml PEA seemed abolish the anti-inflammatory effect seen with PEA alone.

Figure 5:
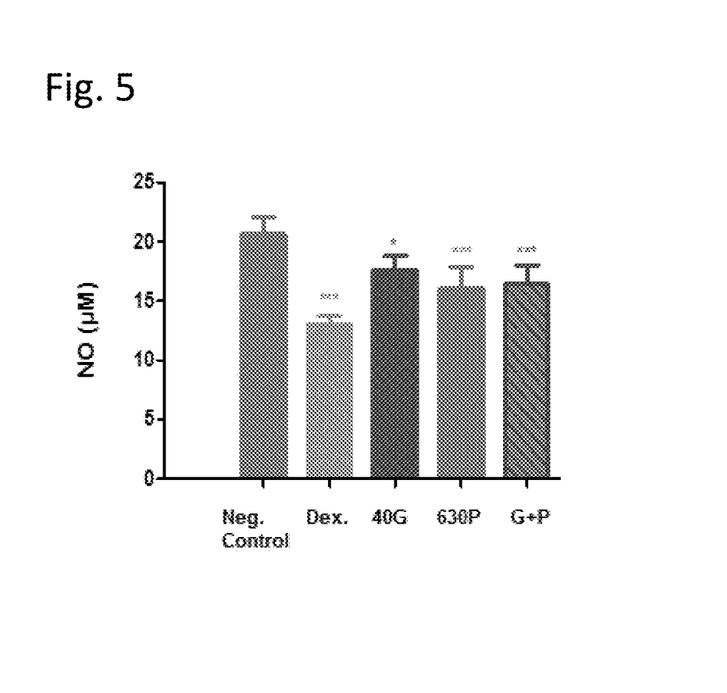
FIG. 5 graphically presents the results for a binary combination of *Ginkgo biloba* and PEA at the same concentrations as used to generate the results for the synergistic three-component composition in FIG. 3.

Similarly, it may be seen in FIG. 5 that while both 40 µg/ml *Ginkgo biloba* and 630 µg/ml PEA each cause a certain degree of NO release inhibition when tested separately, the addition of *Ginkgo biloba* to PEA did not numerically increase the inhibitory effect. In other words, the binary combination of these two substances yielded a result that was even less than additive.

Figure 6:
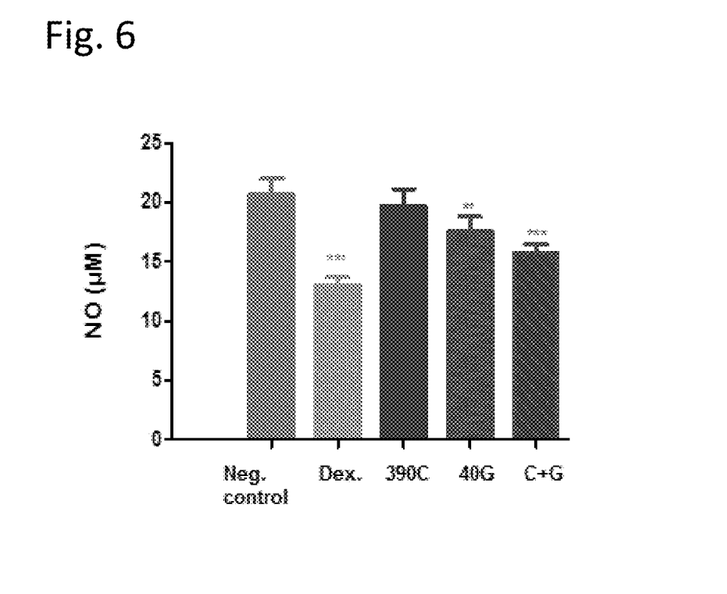
FIG. 6 presents the results for a binary combination of caffeine and *Ginkgo biloba* at the same concentrations as used to generate the results for the synergistic three-component composition in FIG. 3.

Finally, it may be observed in FIG. 6 that a combination of 390 µg/ml caffeine and 40 µg/ml *Ginkgo biloba* did cause a greater inhibitory effect on this model of inflammation than either of those two substances when tested individually at the indicated concentrations. However, this appears to be an additive rather than synergistic effect. Furthermore, the degree of inhibition caused by this combination is numerically less than the dexamethasone positive control. This contrasts with the greater-than-positive-control effect seen with the three-component combination of FIG. 3.

Consideration of the results shown in FIGS. 3-6 leads to the following conclusions.

In the model of inflammation used:

A) No synergism between PEA and *Ginkgo biloba* was observed.

B) No synergism between caffeine and PEA was observed.

C) There is probably only an additive (rather than synergistic) interaction between caffeine and *Ginkgo biloba*.

D) It therefore unexpectedly appears that all three components are necessary in order to see the high level of synergy shown in FIG. 3 of the application. It was not possible to predict this result from the results obtained with the individual agents, tested alone, or with the results obtained with binary pairs of said agents.

It may be concluded from these studies that there is an unexpected synergistic interaction between caffeine, *Ginkgo biloba* and PEA with regard to an in vitro model of inflammation, when these agents are combined at various different weight ratios.

II. Formulations Containing Compositions of the Present Invention

Example 2

Immediate Release Tablets

Mix together 2 kg standardized herbal extract of *Ginkgo biloba* with 6.6 kg PEA.HCl and 1.3 kg caffeine, all components being milled until a particle size distribution (PSD) of 100-250 micron was achieved.

Add 5 kg microcrystalline cellulose PH 102 and 100 g Syloid and mix for 10 minutes Add 50 g magnesium stearate and mix for 10 minutes.

Preparing Tablets in Two Strengths

1. Compress the resulting mixture into tablets, each tablet comprising 150 mg *Ginkgo biloba,* 500 mg PEA.HCl and 100 mg caffeine.

2. Compress the resulting mixture into tablets, each tablet comprising 75 mg *Ginkgo biloba,* 250 mg PEA.HCl and 50 mg caffeine.

Example 3

Tablets Containing Part of the *Ginkgo biloba* Component in Extended Release Form Coat 1 Kg standardized herbal extract of *Ginkgo biloba* with Ethocel™. 10 cp in a ratio of 9:1 *Ginkgo biloba*/Ethocel™. The coating can be done in a fluidized bed via top or bottom spray granulation.

Mix together 1 kg standardized herbal extract of *Ginkgo biloba* and 1 kg of the Ethocel™ coated *Ginkgo biloba* from above with 6.6 kg PEA.HCl and 1.3 kg caffeine, all components being milled to a PSD of between 100 and 250 micron.

Add 5 kg microcrystalline cellulose PH 102 and 100 g Syloid and mix for 10 minutes Add 50 g magnesium stearate and mix for 10 minutes.

Preparing Tablets in Two Strengths

1. Compress the resulting mixture into tablets, each tablet comprising 150 mg *Ginkgo biloba,* 500 mg PEA.HCl and 100 mg caffeine.

2. Compress the resulting mixture into tablets, each tablet comprising 75 mg *Ginkgo biloba,* 250 mg PEA.HCl and 50 mg caffeine.

Example 4

Extended Release Tablets (All of *Ginkgo biloba* Formulated for Extended Release)

Coat 2 Kg standardized herbal extract of *Ginkgo biloba* with Ethocel™ 10 cp in a ratio of 9:1 *Ginkgo*/Ethocel™. The coating can be done in a fluid bed via top or bottom spray granulation.

Mix together 2 kg of the Ethocel™ coated *Ginkgo* with 6.6 kg PEA.HCl and 1.3 kg caffeine, all components being milled to a PSD of 100-250 micron.

Add 5 kg microcrystalline cellulose PH 102 and 100 g Syloid and mix for 10 minutes Add 50 g magnesium stearate and mix for 10 minutes.

Preparing Tablets in Two Strengths

1. Compress the resulting mixture into tablets, each tablet comprising 150 mg *Ginkgo biloba,* 500 mg PEA.HCl and 100 mg caffeine.

2. Compress the resulting mixture into tablets, each tablet comprising 75 mg *Ginkgo biloba,* 250 mg PEA.HCl and 50 mg caffeine.

Example 5

Enteric Coated Tablets Containing Extended Release *Ginkgo biloba* Component

Coat 1 Kg standardized herbal extract of *Ginkgo biloba* with Ethocel™ 10 cp in a ratio of 9:1 *Ginkgo*/Ethocel™. The coating can be done in a fluid bed via top or bottom spray granulation.

Mix together 1 kg standardized herbal extract of the coated *Ginkgo biloba* with 6.6 kg PEA.HCl and 1.3 kg caffeine, all components being milled to a PSD of 100-250 micron.

Add 5 kg microcrystalline cellulose PH 102 and 100 g Syloid and mix for 10 minutes Add 50 g magnesium stearate and mix for 10 minutes.

Preparing Tablets in Two Strengths

1. Compress the resulting mixture into tablets, each tablet comprising 150 mg *Ginkgo biloba,* 500 mg PEA.HCl and 100 mg caffeine.

2. Compress the resulting mixture into tablets, each tablet comprising 75 mg *Ginkgo biloba,* 250 mg PEA.HCl and 50 mg caffeine.

Coat the tablets with 8% w/w sodium alginate in order to obtain enteric coated tablets Example 6

Tablets Containing Extended Release *Ginkgo biloba* Component and Caffeine in the Form of Guarana Coat 1 Kg standardized herbal extract of *Ginkgo biloba* with Ethocel™ 10 cp in a ratio of 9:1 *Ginkgo biloba*/Ethocel™. The coating can be done in a fluid bed via top or bottom spray granulation.

Mix together the coated *Ginkgo biloba* with 6.6 kg PEA.HCl and 1.3 kg guarana, all components being milled to a PSD of 100-250 micron.

Add 5 kg microcrystalline cellulose PH 102 and 100 g Syloid and mix for 10 minutes Add 50 g magnesium stearate and mix for 10 minutes.

Preparing Tablets in Two Strengths

1. Compress the resulting mixture into tablets, each tablet comprising 150 mg *Ginkgo biloba,* 500 mg PEA.HCl and 100 mg guarana.

2. Compress the resulting mixture into tablets, each tablet comprising 75 mg *Ginkgo biloba,* 250 mg PEA.HCl and 50 mg guarana.

III Preclinical Studies Concerning the Treatment of Psychological/Psychiatric Disorders in Laboratory Animals.

A series of preliminary investigations were performed in laboratory mice in order to investigate the potential use of the composition of the present invention in the treatment of various disorders having psychological or behavioral components.

Two different compositions of the present invention were tested in these preclinical studies: "STIM1" and "STIM2". A liquid suspension of each of these two compositions was prepared as follows:

STIM1:

200 g of standardized herbal extract of *Ginkgo biloba,* 200 g of PEA HCl, 50 g of caffeine, 450 g of ginseng and 100 g of guarana were mixed together and the resulting mixture milled to a PSD in the range of 100-250 micron. The milled mixture was then suspended in 100 ml water and 0.05-0.4 ml of the obtained suspension was administered to each mouse.

STIM2:

320 g of standardized herbal extract of *Ginkgo biloba,* 470 g of PEA HCl, 160 g of caffeine and 50 g ginseng were mixed together and the resulting mixture milled to a PSD in the range of 100-250 micron. The milled mixture was then suspended in 100 ml water and 0.05-0.4 ml of the obtained suspension was administered to each mouse.

Example 7

Effect of a Single Dose of a Composition of the Present Invention vs. Methylphenidate on Short Term Memory in an Object Recognition Test Short term memory was assessed using an object recognition test. This test assesses the ability of the animals to remember previous exposure to a familiar object, by means of measuring the increase in exploration time of a familiar object (as opposed to the exploration time of a novel object). Further details of this test may be found in many publications, including E. Moscardo et al. [Proceedings of Measuring Behavior 2012 (Utrecht, The Netherlands, Aug. 28-31, 2012)].

In the present study, two groups of laboratory mice received either oral doses of STIM1 (5 animals) or vehicle (5 animals) and 60 minutes later were subjected to a two sessions test. Animals were placed into an arena and exposed to two identical objects (A1 and A2) and allowed to explore for 5 minutes. The time that the animal explored each object was measured.

The mice were then removed to their home cage for 15 minutes and re-placed in the arena, presented with object (A1) and a novel object (B) and allowed to explore them for 5 minutes.

The mean difference in exploration time (i.e. between the familiar object and the unfamiliar object) in the second part of the study was approximately 14 seconds following treatment with STIM1 and approximately 7.5 seconds with the vehicle control group (a statistically significant difference; $p<0.05$; unpaired t-test).

These results indicate that STIM1 is capable of improving short memory to a significantly greater extent than vehicle control.

Example 8

Effects of Compositions of the Present Invention on Exploratory Behavior in C57BL/6 Mice In this study, a comparison was made between the effects of two compositions of the present invention—STIM1 and STIM2—and an inactive herbal composition (negative control) on the exploratory behavior of C57BL/6 mice in a model of Open Field spontaneous activity. In this model, spontaneous locomotor activity of the mice was assessed by means of individually placing the animals in the center of a box and allowing them to freely explore for a defined length of time. Further details of this test, and of its significance in the assessment of anxiety may be found in Belviranli et al. [Proceedings of Measuring Behavior 2012 (Utrecht, The Netherlands, Aug. 28-31, 2012)].

In the present study, two separate types of test were performed:

a. Effect of a single dose of STIM1 or STIM2 on Open Field spontaneous activity: Open field spontaneous activity was recorded during a 30-min session. Tested compositions were administered orally and 30 minutes later, mice were placed in the center of the tested arena for a total time of 30 minutes. Each treatment group consisted of 8 mice.

Both STIM1 and STIM2 reduced the anxiety-like behavior of the mice (i.e. average distance traveled in the margins of the open field out of the total distance traveled per minute), when compared with the vehicle-only negative control. In the case of STIM1 treatment the value for the anxiety-like behavior was 0.7, as opposed to 0.8 for the vehicle control (p<0.05; unpaired t-test). Similar values were obtained for STIM2 treatment.

b. Effect of repeated dose of stimulant on Open Field spontaneous activity

Open field spontaneous activity was recorded during a 30-min session using the TruScan photo beam activity system. C57BL mice (n=5/6 per group) were treated orally with Vehicle (water for injection), Stimulant (STIM1) (170 mg/kg), inactive herbal component control or STIM2 for 5 consecutive days, then 30 minutes after final dosing were placed in the center of 43×43×40 cm arena.

The results indicate that repeated-dose treatment with either STIM1 or STIM2 significantly reduced anxiety-like behavior, without development of tolerance. The results for STIM1 treatment and vehicle-only were 0.7 and 0.82, respectively (p<0.01; unpaired t-test). Similar values were obtained for STIM2 treatment.

These results from both of these tests indicate that the compositions of the present invention may possess significant anxiolytic activity.

IV Pilot Clinical Study Concerning the Treatment of ADHD in Adult Human Subjects.

Example 9

Pilot Study of the Use of a Composition of the Invention to Treat ADHD

Methods:

A randomized, single-blind, dose titration, 7-week treatment phase, outpatient study that evaluates the efficacy of a composition of the present invention in 10 adults (18 to 55 years) previously diagnosed with ADHD.

The composition used in this study was prepared in the form of an orally-administrable caplet containing the following active ingredients:

50 mg Caffeine
300 mg Ginkgo biloba
150 mg PEA

The study had two phases. During the first phase, patients started treatment with a single-blind (patient-blind) 2 weeks' dose titration period, during which, each patient initially received one half caplet per day. If no adverse effects reported, the dosage was raised to a total of one caplet per day. an increase of additional half caplet (a total dose of 1 caplet). Following this, the dose was then increased to a maximum of two caplets per day toward the end of this titration phase.

The initial increase in dosage (from half caplet to one caplet) was achieved on the basis of the patients' own initiative (patients were instructed to call in case the pre-planned escalation was not followed). The further increase in dosage was performed following a clinic visit and at the discretion of the investigator based on the clinical effects on ADHD and on the appearance of any side effects.

Following the completion of this two-week titration phase, the selected dose (highest individually titrated dose) was maintained for an additional 5 weeks (maintenance phase). The study therefore ended a maximum of seven weeks (i.e. 49 days) following the beginning of the dose titration.

Primary patient recorded outcomes:

The primary efficacy measure was the ADHD-RS-IV (assessing adult ADHD symptoms) taken at screening, baseline (after washout of prior treatment), and study efficacy visits.

Time of endpoint evaluation was defined as the last post-randomization treatment week with a valid ADHD-RS-IV score. The primary efficacy endpoint was the mean change from baseline to time of endpoint in ADHD-RS-IV total score in the overall efficacy (PP) or intention-to-treat (ITT) population.

Secondary patient recorded outcomes:

The secondary endpoints included:

Clinical Global Impressions (CGI) scale evaluated global ADHD illness severity and improvement.

CGI-Severity (CGI-S) assessed at baseline used a 7-point scale with scores ranging from 1 (normal, not at all ill) to 7 (among the most extremely ill), in accordance with the following list:

1=normal, not at all ill; 2=borderline mentally ill; 3=mildly ill; 4=moderately ill;
5=markedly ill; 6=severely ill; 7=among the most extremely ill patients Definitions and criteria for analysis of clinical response and symptomatic remission:

| TERMS | DEFINITIONS AND CRITERIA |
| --- | --- |
| Clinical response | ≥30% reduction in ADHD-RS-IV with adult prompts total score (relative to baseline ADHD-RS-IV total score) and a CGI-I rating of 1 or 2 |
| Symptomatic remission | ADHD-RS-IV total score ≤ 18 (average per-item score ≤ 1) |
| Time to median clinical response or symptomatic remission | Time by which criteria for clinical response or symptomatic remission is achieved Time by which half the original sample achieves criteria for clinical response or symptomatic remission |

Safety

Safety assessments was presented for the overall safety population (ITT) and included treatment-emergent adverse events (TEAEs), vital signs and laboratory findings. Absolute values (measurements) as well as changes from baseline for safety parameters were also presented.

Study Results:

All measurements and assessments were performed 7, 14, 28 and 49 days after the beginning of the trial. In addition, the following two separate baseline assessments were performed for each subject:

Baseline measurement 1 (taken during the initial patient screening period; indicated as "BM1" in FIGS. 5, 7, 9 and 10).

Baseline measurement 2 (taken immediately before initial dosage; indicated as "BM2" in FIGS. 5, 7, 9 and 10).

Figure 7:
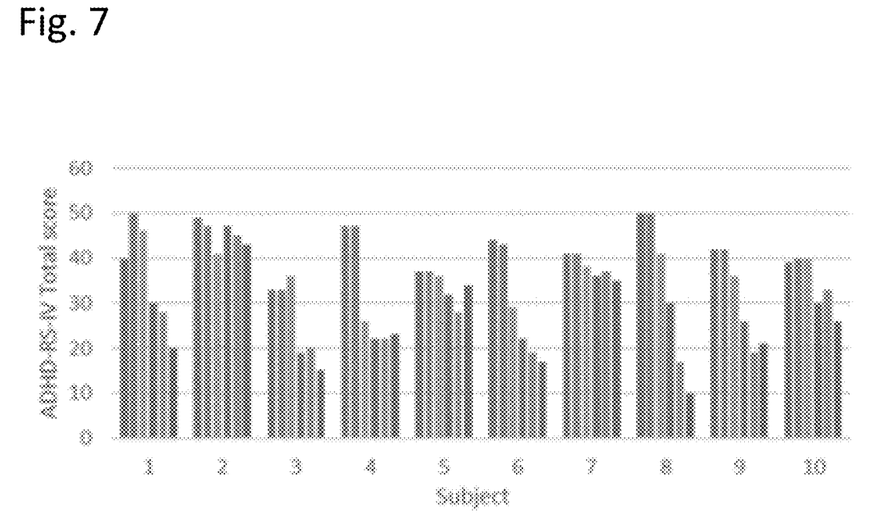
FIG. 7 presents the ADHD score for each of the 10 subjects taking part in the pilot clinical study.
Figure 8:
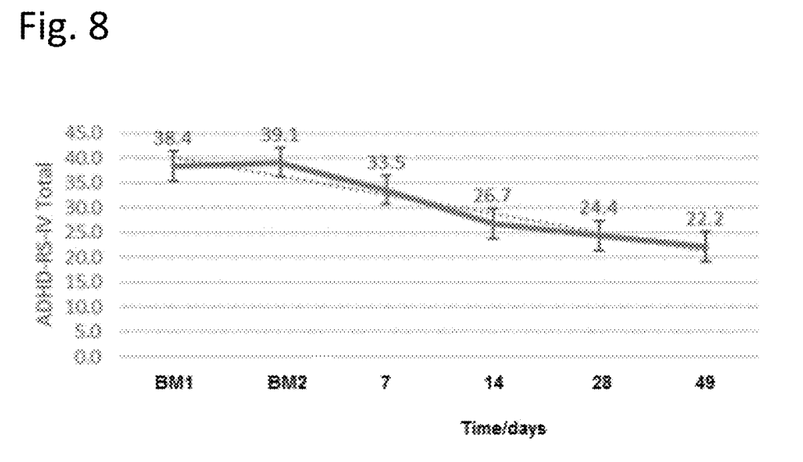
FIG. 8 presents the results for the ADHD score in the pilot clinical trial subjects taken as a group.
Figure 9:
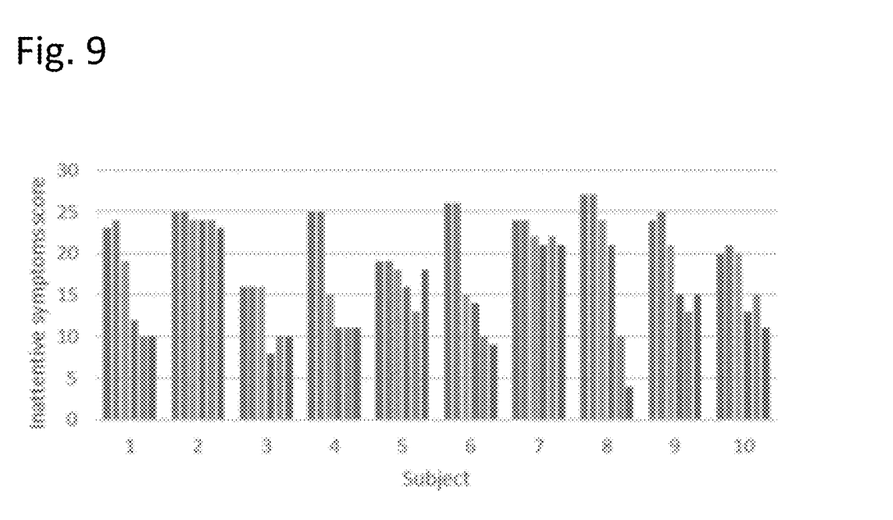
FIG. 9 graphically depicts the Inattentive Symptom Score for each of the 10 subjects participating the pilot study.

FIGS. 4-10 graphically show the results of the various measurements and assessments described above. In FIGS. 4, 6 and 8, the multiple bars represent, from left to right, the following time points: baseline measurement 1, baseline measurement 2, day 7, day 14, day 28 and day 49.

ADHD-RS-IV Total Score:

As shown in FIG. 7, individual data analysis revealed that out of 10 treated patients, significant improvement in ADHD score could be demonstrated in 7 patients and a moderate effect in one more patient.

The results for ADHD score in the subjects taken as a group are graphically presented in FIG. 8. It may be seen from these results that treatment with the composition reduced ADHD severity by 43%. This effect was seen almost immediately following administration of the composition (as evidenced by the group result at the 7-day time point). The therapeutic effect accumulated and there was no development of tolerance. The maximum effect was seen on day 49.

ADHD-RS-IV Inattentive Symptom Score:

The 'predominantly inattentive subtype' is similar to the other presentations of ADHD and is characterized primarily by problems with inattention or a deficit of sustained attention, such as procrastination, hesitation, and forgetfulness. As shown in the individual data plotted in FIG. 9, out of 10 treated patients 7 showed a remarkable improvement in this subset of symptoms, while some effect could also be demonstrated in 2 further patients.

Figure 10:
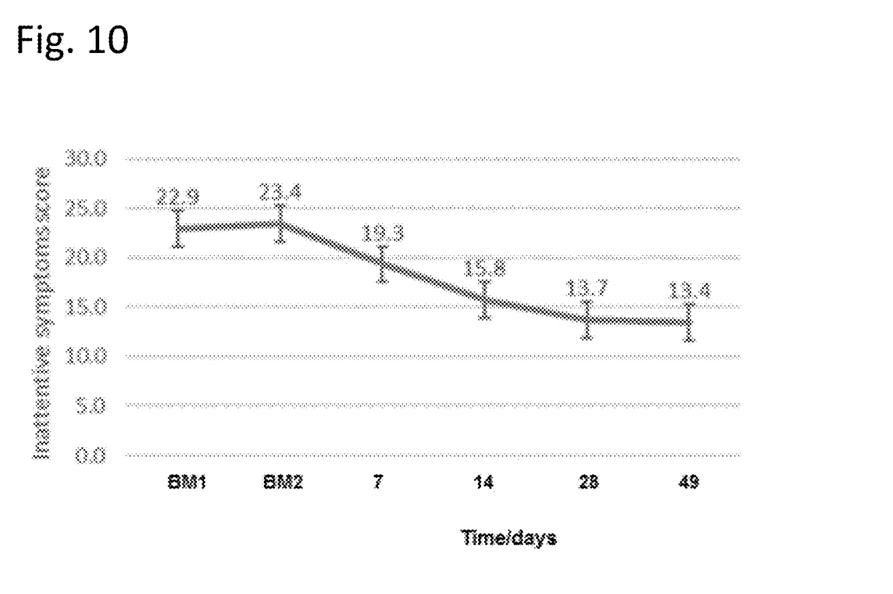
FIG. 10 presents the group results for the Inattentive Symptom Score.

The group results for the inattentive score are shown in the line graph presented in FIG. 10. A significant (40%) reduction in this score was seen following administration of the composition of the invention. The maximum effect was seen on day 49 of treatment.

Figure 11:
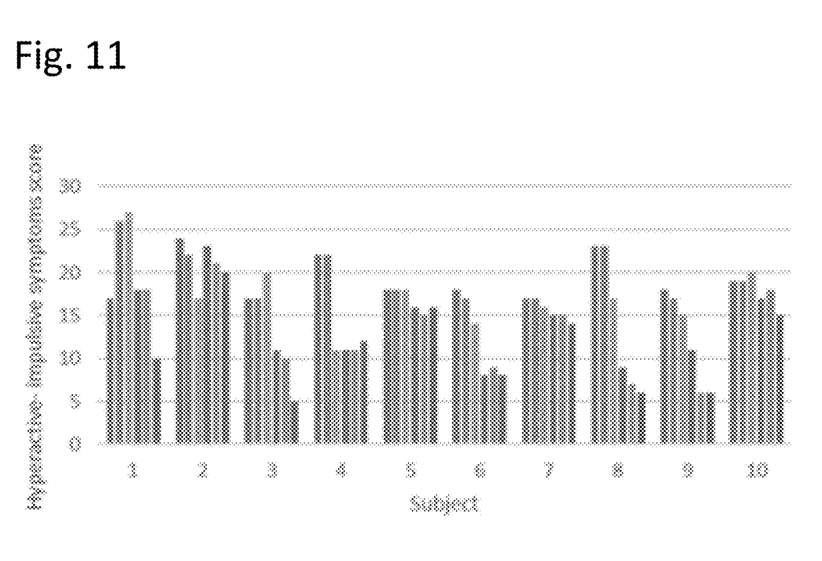
FIG. 11 graphically presents the Hyperactive-Impulsive Symptom Score for each of the 10 subjects included in the pilot clinical study.

ADHD-RS-IV Hyperactive-impulsive symptoms Score:

The hyperactive-impulsive symptom score data for individual subjects are shown in FIG. 11. It may be seen from this graph that a marked effect on hyperactivity-impulsive symptoms could be demonstrated in 6 patients while a mild moderate effect could be demonstrated in the remaining 4 patients.

Figure 12:
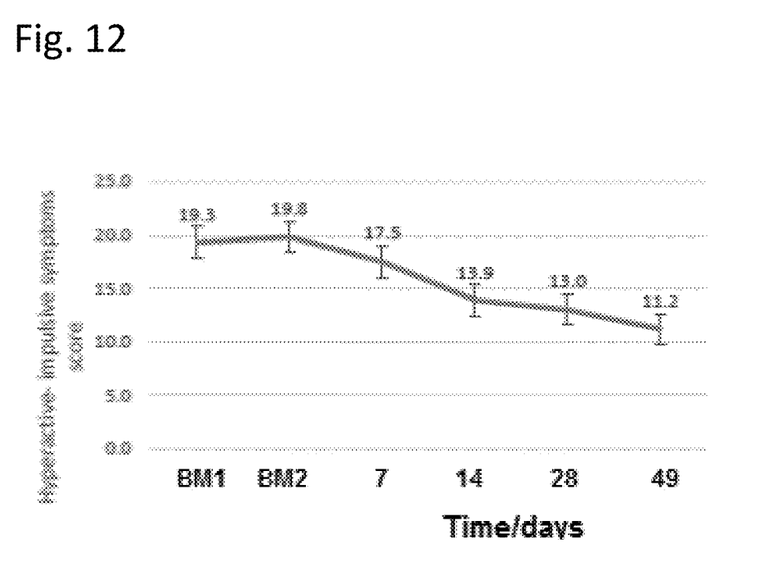
FIG. 12 presents the group results for the Hyperactive-Impulsive Symptom Score.

The group results for the hyperactive-impulsive symptoms are shown in FIG. 12. In common with the observed effect on the initiative symptoms, treatment with the composition of the invention markedly reduced the severity of hyperactivity symptoms reaching a maximum reduction of ~40% by day 49.

Figure 13:
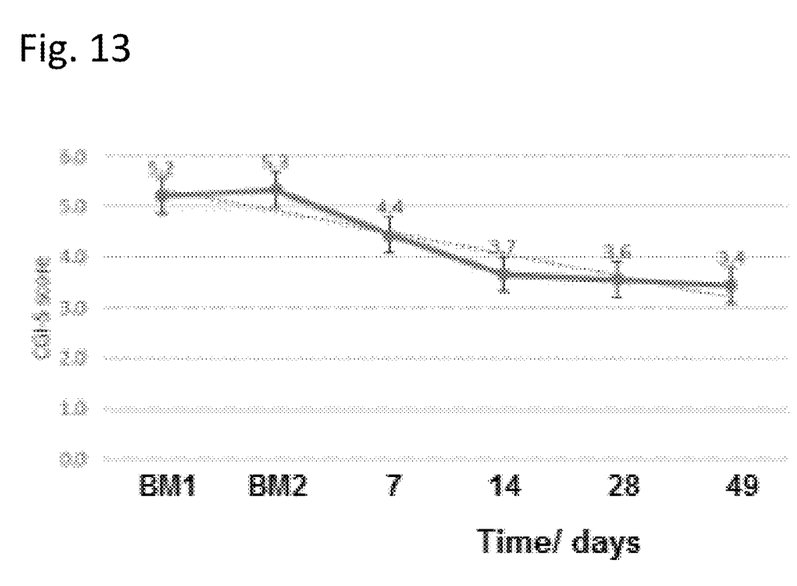
FIG. 13 presents the group results for the Clinical Global Impressions (CGI) severity scale average.

Clinical Global Impressions (CGI) Severity Scale Group Average:

The group results for this parameter are shown in FIG. 13. It will be noted that the improvement in ADHD symptoms (reported above and shown in FIGS. 4-9) was well correlated with a significant improvement (34%) in the patients' clinical global impressions scale.

Conclusions:

This pilot study clearly demonstrates that treatment with the composition of the invention was well tolerated and was not accompanied by any of the adverse side effects such as weight loss etc. that are associated with the administration of known chemically-based stimulant medications.

Furthermore, most of the patients treated with the composition of the present invention showed a substantial (within the range of 40%) improvement in their ADHD symptoms. This was well correlated with an improvement in patients clinical score.

The invention claimed is:

1. A unit dosage form comprising 10-200 mg of caffeine, 50-500 mg of *Ginkgo biloba*, and 50-1000 mg of β-phenylethylamine (PEA) or its salt, wherein the weight ratio between the caffeine, *Ginkgo biloba*, and PEA or its salt is in the range of 1 caffeine: 0.1-10 *Ginkgo biloba:* 1-15 PEA.

2. The unit dosage form according to claim 1, further comprising actives selected from the group consisting of guarana, ginseng, kaempferol, curcumin, licorice, Amur Corktree (*Phellodendron amurense*), licorice root (*Glycyrrhiza glabra* and *Glycyrrhiza uralensis*), Psoralea Fruit (*Psoralea corylifolia*) and Bakuchi seed (*Cyamposis psoralioides*) and combinations thereof.

3. The unit dosage form according to claim 1, wherein the weight ratio between the caffeine, *Ginkgo biloba*, and PEA or its salt is in the range of 1 caffeine: 2-8 *Ginkgo biloba:* 1.5-5 PEA.

4. The unit dosage form according to claim 1, wherein the weight ratio between the caffeine, *Ginkgo biloba*, and PEA or its salt is 1 caffeine: 6 *Ginkgo biloba:* 3 PEA.

5. The unit dosage form of claim 1, formulated in the form of tablets, caplets, capsules, powders, sachets for suspension or dispersible tablets to be added to water.

6. The unit dosage form according to claim 1, which is an oral dosage form.

7. The unit dosage form according to claim 6, further comprising one or more pharmaceutical excipients.

8. The unit dosage form according to claim 6, wherein all of the active components are formulated for immediate release.

9. The unit dosage form according to claim 6, wherein at least a portion of the *Ginkgo biloba* is formulated for controlled release.

10. The unit dosage form according to claim 1, wherein the weight ratio between PEA and *Ginkgo biloba* is between about 0.1:1 and 20:1.

11. The unit dosage form according to claim 1, wherein the weight ratio between PEA and *Ginkgo biloba* is between about 0.5:1 and 16:1.

12. The unit dosage form according to claim 1, wherein the weight ratio between PEA and caffeine is between about 1:1 and 20:1.

13. The unit dosage form according to claim 1, wherein the weight ratio between PEA and caffeine is between about 1.5:1 to 15:1.

14. The unit dosage form according to claim 1, comprising 30-200 mg of caffeine.

15. A unit dosage form comprising 30-200 mg of caffeine, 50-500 mg *Ginkgo biloba*, and 50-1000 mg of β-phenylethylamine (PEA) or its salt.

16. The unit dosage form according to claim 15, comprising 40-100 mg of caffeine, 100-500 mg *Ginkgo biloba*, and 100-200 mg of PEA or its salt.

17. The unit dosage form according to claim 15, comprising 50 mg of caffeine, 300 mg *Ginkgo biloba*, and 150 mg of PEA or its salts.

* * * * *